US012650424B2

(12) United States Patent
Dahoun et al.

(10) Patent No.: US 12,650,424 B2
(45) Date of Patent: Jun. 9, 2026

(54) METHOD AND SYSTEM FOR DETERMINING INTRACELLULAR MEDIATORS' ACTIVITY

(71) Applicant: ECOLE POLYTECHNIQUE FEDERALE DE LAUSANNE (EPFL), Lausanne (CH)

(72) Inventors: Thamani Dahoun, Lausanne (CH); Margaux Duchamp, Lausanne (CH); Philippe Renaud, Preverenges (CH); Marc Brugarolas, Pampigny (CH); Horst Vogel, Preverenges (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 572 days.

(21) Appl. No.: 18/007,501

(22) PCT Filed: Jun. 23, 2021

(86) PCT No.: PCT/EP2021/067241
§ 371 (c)(1),
(2) Date: Dec. 1, 2022

(87) PCT Pub. No.: WO2022/008254
PCT Pub. Date: Jan. 13, 2022

(65) Prior Publication Data
US 2023/0221301 A1 Jul. 13, 2023

(30) Foreign Application Priority Data
Jul. 7, 2020 (EP) .................................... 20184533

(51) Int. Cl.
*G01N 33/543* (2006.01)
*G01N 33/50* (2006.01)

(52) U.S. Cl.
CPC ....... *G01N 33/5041* (2013.01); *G01N 33/543* (2013.01); *G01N 2333/4719* (2013.01); *G01N 2333/4724* (2013.01); *G01N 2333/726* (2013.01)

(58) Field of Classification Search
CPC ................................................... G01N 33/543
See application file for complete search history.

(56) References Cited

FOREIGN PATENT DOCUMENTS

EP 1668161 A2 6/2006

OTHER PUBLICATIONS

Stratagene Catalog, 1988, p. 39.*
Agarose Bead Technologies, pp. 1-3, 2024.*
International Search Report from corresponding PCT Application No. PCT/EP2021/067241 dated Oct. 12, 2021.
Written Opinion from corresponding PCT Application No. PCT/EP2021/067241 dated Oct. 12, 2021.
Roizard, S., et al., "Activation of G-Protein-Coupled Receptors in Cell-Derived Plasma Membranes Supported on Porous Beads," Journal of the American Chemical Society, 133: 16868-16874 (2011).
Danelon, C., et al., "Probing the function of ionotropic and G protein-coupled receptors in surface-confined membranes," Methods, 46: 104-115 (2008).
Decrop, D., et al., "Optical Manipulation of Single Magnetic Beads in a Microwell Array on a Digital Microfluidic Chip," Anal. Chem., 88: 8596-8603 (2016).
Tirapu-Azpiroz, J., et al., "Arraying single microbeads in microchannels using dielectrophoresis-assisted mechanical traps," Applied Physics Letters, 107: 1-4 (2015).

* cited by examiner

*Primary Examiner* — Prema M Mertz
(74) *Attorney, Agent, or Firm* — Harness Dickey & Pierce P.L.C.

(57) ABSTRACT

A method for determining the presence of a molecule coupled to the cytoplasmic side of a cellular membrane is disclosed. The method is implemented in a microfluidic setting and is particularly suitable for determining the presence and/or the activity of a G protein or an arrestin protein in a cell.

14 Claims, 9 Drawing Sheets

METHOD AND SYSTEM FOR DETERMINING INTRACELLULAR MEDIATORS' ACTIVITY

PRIORITY STATEMENT

This application is a national stage application under 35 U.S.C. § 371 of PCT International Application No. PCT/EP2021/067241, which has an international filing date of 23 Jun. 2021 and claims priority under 35 U.S.C. § 119 to European Patent Application No. 20184533.6 filed on 7 Jul. 2020. The contents of each application recited above are incorporated herein by reference in their entirety.

TECHNICAL FIELD

The invention belongs to the field of biochemistry. In particular, the invention describes methods and systems for assessing the presence of intracellular mediators coupled to the inner side of cellular membranes, such as $G\alpha$ proteins, and/or activity of biomolecules coupled thereto.

BACKGROUND ART

G protein-coupled receptors (GPCRs) represent approximately 4% of the human genome and constitute the largest family of cell surface membrane receptors[1]. Due to their ability to transduce a wide variety of extracellular signals (photons, mechanical stress, hormones, growth factors, neurotransmitters, odors) to the intracellular compartment[2], they are involved in many central physiological processes and are among the most important therapeutic targets for different diseases[3-8] (Table 1).

As summarized in FIG. 1, an activating ligand binds to and switches its cognate GPCR to an active conformation, which now is competent to interact with a heterotrimeric G-protein to mediate their actions.

The molecular interactions that occur between the receptor and the G protein are fundamental to the transduction of environmental signals into specific cellular responses. The G proteins themselves play important roles in determining the specificity and temporal characteristics of the cellular response to the ligand-binding signal. In the inactive state, G proteins are heterotrimeric, consisting of one $\alpha$, one $\beta$ and one $\gamma$ subunit, and a bound deoxyguanosine diphosphate (GDP). Receptor-catalyzed guanine nucleotide exchange resulting in deoxyguanosine triphosphate (GTP) binding to the a subunit activates the G protein. $G\alpha$-GTP dissociates from the $G\beta\gamma$ subunits, allowing the $G\beta\gamma$ dimer and the $G\alpha$-GTP subunit each to activate downstream effectors[9-11]. Hydrolysis of GTP to GDP deactivates the complex and turns off the cellular response.

Different ligands can activate different cellular signaling pathways which are mediated by distinct G-proteins classified as $G\alpha_s$, $G\alpha_{i/o}$, $G\alpha_{q/11}$ or $G\alpha_{12/13}$ subfamilies[12,13]. An essential GTPase domain where the nucleotide GDP/GTP exchange occurs after GPCR activation[14] is common to the $G\alpha$ subunit of all the four families, however they differ from each other by the different effectors that they activate (FIG. 2): $G\alpha_s$ family triggers the transmembrane adenylyl cyclase (AC) leading to the production of the cAMP second messenger, $G\alpha_{i/o}$ family inhibits the AC resulting in a decrease of cAMP, $G\alpha_{q/11}$ family activates the membrane bound

TABLE 1

Example of GPRCs involved in diseases. GPCR mutations or dysfunctions lead to disorders in different part of the human body.

| GPCR name | Disease association | GPCR name | Disease association |
|---|---|---|---|
| S1P1 receptor | Immune system Multiple sclerosis | CCR5 chemokine receptor | Insulin-dependent diabetes mellitus type 22 |
| D3 Dopamine receptor | Brain signalling Schizophrenia | Melanocortin receptor 4 | Obesity |
| H1 Histamine receptor | Immune system Allergies inflammation | Cannabinoid receptor 1 | Obesity in men |
| CXCR4 chemokine receptor | Immune system HIV Cancer | Cannabinoid receptor 2 | osteoporosis |
| K-opioid | Pain Mood Drug abuse | P2Y purinoreceptor 1 | Thrombosis risk |
| FQ receptor | Pain Mood Drug abuse | P2Y purinoreceptor 1 | Bleeding disorder |
| A2a Adenosine receptor | Cardiovascular disease Respiratory disease Parkinson's disease | Follicle-stimulating hormone receptor | Ovarian hyperstimulation syndrome |
| B2 Adrenergic receptor | Cardiovascular disease Asthma | Lutropin-choriogonadotropic hormone receptor | Leydig-cell tumour |
| CCR2 receptor | Bone metastasis | Thyroid-stimulating hormone receptor | Hyperthyroidism Thyroid carcinoma |
| Rhodopsin | Congenital night blindness Retinitis pigmentosa | GRP52 | Huntington's disease |
| M1 acetylcholine receptor | Schizophrenia | A1 Adenosine receptor | Cognitive deficit |
| Vasopressin V1a receptor | autism | Vasopressin V2a receptor | Nephrogenic diabetes insipidus | phospholipase C (PLC) leading to the production of inositol trisphosphate ($IP_3$) second messenger and then release of intracellular $Ca^{2+}$ and finally the $G\alpha_{12/13}$ family regulates Rho family GTPase[13].

In addition to signaling through G-proteins, GPCRs can signal through arrestins. Arrestins were first described as proteins that turn off G-protein signaling: Phosphorylation of the receptor C-terminal tail by a G protein-linked kinase leads to recruitment of arrestin, which prevents interaction with G proteins and promotes receptor internalization. However, certain GPCR ligands can activate arrestin binding directly or possibly by promoting interaction with kinases that phosphorylate the receptor to enable arrestin binding, thereby activating downstream signaling pathways distinct from those mediated by G proteins[11].

The detection and analysis of cellular signalling mediated by GPCRs are of importance in the following fields:

a) in fundamental research for elucidating the mechanism of GPCR mediated signal transduction reactions involved in physiological and pathophysiological conditions;

b) for biomedical applications to diagnose diseases related to disorders in GPCR signalling;

c) for developing novel medicines to treat diseases which are related to disorders in GPCR signalling;

d) for developing new compounds which are inducing cell differentiation to be used in biomedical or biotechnological applications;

e) for developing compounds which would act as new flavour, fragrance and nutritional ingredients by influencing olfactory or gustatory GPCR chemosensory system.

Over the past years, three major types of assays to monitor signaling of G-proteins mediated by activated GPCRs have been developed: (1) indirect assays measuring production of effectors and second messengers; (2) direct assays monitoring the nucleotide exchange at the G-protein or the interaction between the receptor and the G-protein itself (see Table 2); (3) label-free whole-cell biosensing measure the optical or electrical properties of the interface between a solid sensor support and biological cells, which are changing upon activation of GPCR mediated signaling[15,16].

TABLE 2

Summary of GPCR screening technologies.

| Assay classification | Commonly used assays | Commercial HTS Technology (Company) | Pros | Cons | Suitable GPCRs |
|---|---|---|---|---|---|
| Receptor binding assay | Radioligand binding assay Other tagged-ligand binding | Filtration assay (PerkinElmer) SPA (GE Healthcare or PerkinElmer) DELFIATM TRF (PerkinElmer); LanthaScreenTM system (Invitrogen); Tag-liteTM system (Cisbio) Filtration assay PerkinElmer) SPA (GE Healthcare or PerkinElmer) DELFIATM GTP Binding Assay (PerkinElmer) | High-throughput; less interference; obtain agonist and antagonist in one assay Non-radioactive; high-throughput; obtain agonist and antagonist in one assay | Availability of radioligand; generation of radioactive waste; need secondary functional assay Availability of tagged-ligand; need secondary functional assay | any GPCR any GPCR |
| G-protein dependent assays | GTPγS binding | Filtration assay (PerkinElmer) SPA (GE Healthcare or PerkinElmer) DELFIATM GTP Binding Assay (PerkinElmer) | Functional cell-free assay; discrimination between full or partial agonists, neutral antagonists, inverse agonists, allosteric regulators | Relatively low signal to background window | $G\alpha_{i/o}$ |
| | CRE/MRE reporter assay | | Homogenous assay; high-throughput; large signal to background window | Need to know the coupling mechanism, not good for orphan GPCR | any GPCR |
| | cAMP assay | SPA cAMP assay (GE Healthcare or PerkinElmer) HitHunterTM (DiscoveRx); AlphaScreenTM (PerkinElmer); Fluorescence polarization-based cAMP kits (PerkinElmer, Molecular Devices and GE Healthcare); HTRFTM-based cAMP (Cisbio); cAMP GlosensorTM (Promega) | High-throughput; very sensitive | Need to know the coupling mechanism, not good for orphan GPCR | $G\alpha_s$, $G\alpha_{i/o}$ |
| | $Ca^{2+}$ | Fluo-3 or Fluo-4 (Invitrogen) and FLIPRTM automated real-time fluorescence plate readers (Molecular Device) | High-throughput; functional assay for live cells; obtain agonist, antagonist and allosteric modulator in one assay | Fluorescent interference from compounds; not good for inverse agonist and slow binding agonist | $G\alpha_q$ (with $G\alpha_{15/16}$, could be universal) |
| | $IP_{1/3}$ | SPA $IP_3$ assay (PerkinElmer) AlphaScreen™ (PerkinElmer); HitHunter™ Fluorescence Polarization (DiscoveRx); HTRF IP-One™ (Cisbio) | High-throughput; functional assay for live cells; good for slow binding ligands | Limited industrial validation | $G\alpha_q$ (with $G\alpha_{15/16}$, could be universal) any GPCR |

TABLE 2-continued

| | | Summary of GPCR screening technologies. | | | |
|---|---|---|---|---|---|
| Assay classification | Commonly used assays | Commercial HTS Technology (Company) | Pros | Cons | Suitable GPCRs |
| G-protein independent assays | Receptor trafficking | Cellomics ArrayScan ™ (Thermo Scientificf); INCell ™ Analyzer 3000 (GE Healthcare); Opera ™ (Evotec Technologies); Acumen ™ Explorer (TTP Lab Tech) | Image based, high-content; functional assay for live cells; generic method for all GPCRs | Image based, relatively low throughput | any GPCR |
| | β-Arrestin recruitment assay | TransfluorTM(Molecular Device); BRET/FRET Tango ™ (Invitrogen); PathHunter ™ (DiscoveRx); | High-throughput; image or non-image based; functional assay for live cells; useful in biased signal detection; generic method for all GPCRs | Affinity for β-arrestin binding varies amone GPCRs; less sensitive; need further pathway analysis | any GPCR |
| | Label-free assay | BIND ™ RWG biosensors (SRU Biosystems) Epic ™ RWG biosensors systems (Corning Inc); ECISTM (Applied Biophysics); xCELLigence ™ System (Roche and ACEA Biosciences) CellKey ™ (MDS) | Label-free functional assay in native live cells; summation of all cellular events | Possibly higher false positive and false negative rates; need special instrument and costly microplate; need further pathway analysis | any GPCR |
| Receptor dimerization assay | | BRET/FRET; PathHunter ™ (DiscoveRx); Tag-liteTM (Cisbio) | GPCR heterodimers are considered new pharmacological targets | Very artificial system, can not assess GPCR dimerization in native state | any GPCR |

Indirect assays comprise the measurement of intracellular cAMP, the measurement of intracellular calcium or the detection of the inositol triphosphate (IP$_3$) produced after GPCR induction with compounds. Different assays exist for the detection of intracellular cAMP such as fluorescent or luminescent enzymatic biosensor, scintillation proximity assay (SPA) or assay using the recombinant exchange protein directly activated by cAMP (EPAC)[17]. To measure the intracellular calcium release, the use of a sensitive fluorescent dye is the most common assay as it is optimized for automated real-time fluorescence plate reader but the recombinant expression of the jellyfish photoprotein aequorin[18] has been also developed for the screening of GPCRs. Indirect assays include also reporter assays that allow the measurement of GPCR activation via the transcription of different genes (cAMP response element (CRE), nuclear factor of activated T-cells response element (NFAT-RE), serum response element (SRE) fused to a reporter protein (FIG. 2). In direct assays, the interaction between the receptor and the G-protein is determined with fluorescence resonance energy transfer (FRET) or bioluminescent resonance energy transfer (BRET) using recombinant fusion proteins on the GPCR and the G protein. The direct activation of GPCRs is also measured with GTPγS binding assays which directly detect the guanine nucleotide exchange of G proteins. In this assay, the accumulation of the non-hydrolysable GTP analogs such as BODIPY-GTPγS or [$^{35}$S]-GTPγS[20] on solubilized plasma membranes is measured after GPCR activation.

Although these methods are widely used, each one has some intrinsic disadvantages: (1) Indirect assays relying on the detection of G-protein activation via the production of second messengers are based on signaling events far downstream from the primary and central interaction process between the activating ligand and its receptor, making the assay prone to unwanted cross-talks and the measured signal complicated. (2) More direct assays require solubilized membranes and generate radioactive waste in the case of [$^{35}$S]-GTPγS binding assay. Alternative direct assays based on fluorescence resonance energy transfer (FRET) require fluorescently labelled proteins genetically engineered and expressed in heterologous cells. (3) For the mentioned label-free biosensing assays, biological cells are immobilized on a solid biosensor surface. The activation of the GPCR signaling cascade induce an overall morphological change in the immobilized cells. This in turn changes the interfacial properties between the sensor and the cell surface, which can be detected either optically by dynamic mass redistribution (DMR)[17,18,] or electrically by cellular dielectric spectroscopy[22,23.] Both biosensing assays measure GPCR signaling indirectly as an overall cellular response in a dose-dependent manner when living cells are exposed to pharmacologically active compounds.

Roizard, S. et al.[25] describes a bioanalytical platform enabling the study of GPCRs in their native membrane transferred inside-out from live cells to lectin-coated beads, with both membrane sides of the receptor being accessible for molecular interactions. The interactions between the different signaling partners during the formation and subsequent dissociation of the ternary signaling complex on single beads could be observed in real time using multicolor fluorescence microscopy. This approach of tethering inside-out native membranes represents a generic platform suitable for ensemble as well as single-molecule measurements to investigate signaling processes at plasma membranes. However, the described method is very laborious, time-consuming due to the immunolabeling and with a relatively poor efficiency due to its in-bulk nature.

The above-mentioned limitations of presently used assay settings show that there is an urgent need for novel assay formats which would efficiently and rapidly monitor GPCR mediated signaling directly on the level of G-protein activation or arrestin signaling based on native (i.e. unmodified) GPCRs and native signaling proteins.

SUMMARY OF INVENTION

In order to address and overcome at least some of the above-mentioned drawbacks of the prior art solutions, the present inventors developed methods and systems for assessing the presence of intracellular mediators coupled to the inner side of cellular membranes, such as Gα proteins, and/or activity of biomolecules coupled thereto, having improved features and capabilities that overcomes or at least reduces the above-summarized drawbacks affecting known solutions according to the prior art.

In particular, a first purpose of the present invention is that of providing a rapid, highly efficient and reproducible assay for assessing the presence of intracellular mediators coupled to the inner side of cellular membranes, such as Gα proteins, and/or activity of biomolecules coupled thereto, such as GPCRs.

A further purpose of the present invention is that of providing a method and system for easily enabling a decoupling between cell treatment, such as a coating, and further steps such as the activation of the membrane receptor experiments, thus opening new opportunities of storage of material and subsequent re-analysis or complementary analysis of samples.

Still a further purpose of the present invention is that of providing a system and method for screening GPCRs activity and/or screening of molecules for an activity on GPCRs that is amenable to miniaturization, automation and high-throughput.

All those aims have been accomplished with the present invention, as described herein and in the appended claims.

Here it is described in one exemplary embodiment a microfluidic assay platform for monitoring directly the activation of distinct, native G proteins induced by ligand binding to native GPCRs using cell-derived plasma membranes immobilized on micrometer sized agarose beads. A microfluidic chip, as well as method steps for using thereof, have been optimized to overcome the above-listed drawbacks of the prior art: arrays of tailor-made traps have been introduced into a microfluidic chip to accommodate and immobilize beads designed to interact with cell plasma membrane fragments.

In view of the above-summarized drawbacks and/or problems affecting solutions known in the art, according to the present invention there is provided a method for determining the presence of a molecule coupled to the cytoplasmic side of a cellular membrane according to claim 1.

Another object of the present invention relates to a kit to perform a method of the invention according to claim 10.

Further embodiments of the present invention are defined by the appended claims.

The above and other objects, features and advantages of the herein presented subject-matter will become more apparent from a study of the following description with reference to the attached figures showing some preferred aspects of said subject-matter.

DETAILED DESCRIPTION OF THE INVENTION

Figure 1:
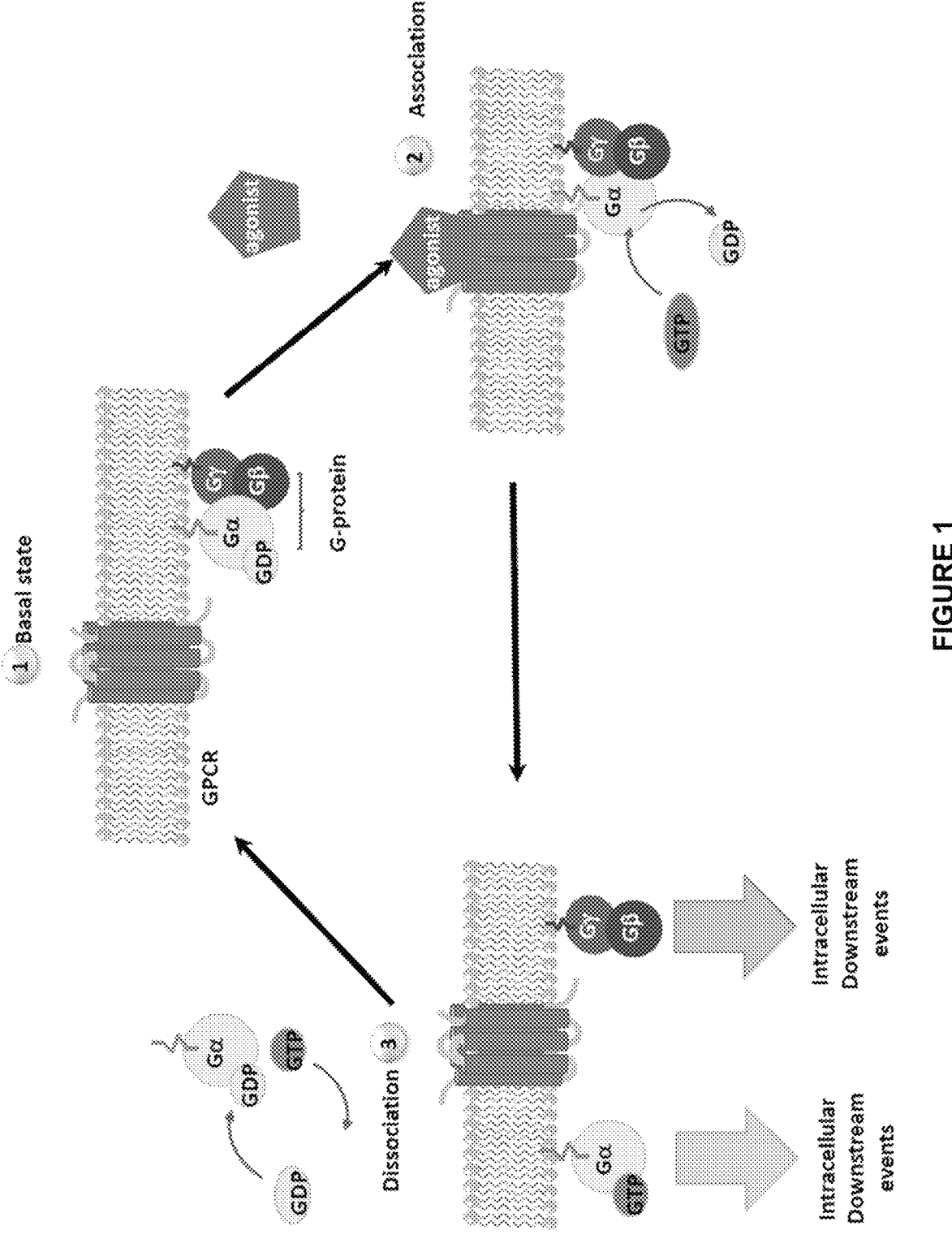
FIG. 1. General scheme for G-protein activation in a mammalian cell. (1) Basal state: GαGDP-βγ heterotrimeric G protein forms a tight inactive complex dissociated from the receptor. (2) Association: activation of the receptor by the agonist promotes recruitment of Gαy to the receptor and the subsequent GDP/GTP exchange at the level of the Gα subunit. (3) Dissociation: nucleotide exchange leads to the dissociation of the receptor and also of the Gα-GTP and Gβγ subunits, which are now able to activate their effectors. The activation cycle is terminated by the Gα intrinsic GTPase activity which allows GTP hydrolysis and the reassociation of Gα-GDP with Gβγ subunits so to restore the inactive basal state (1)
Figure 2:
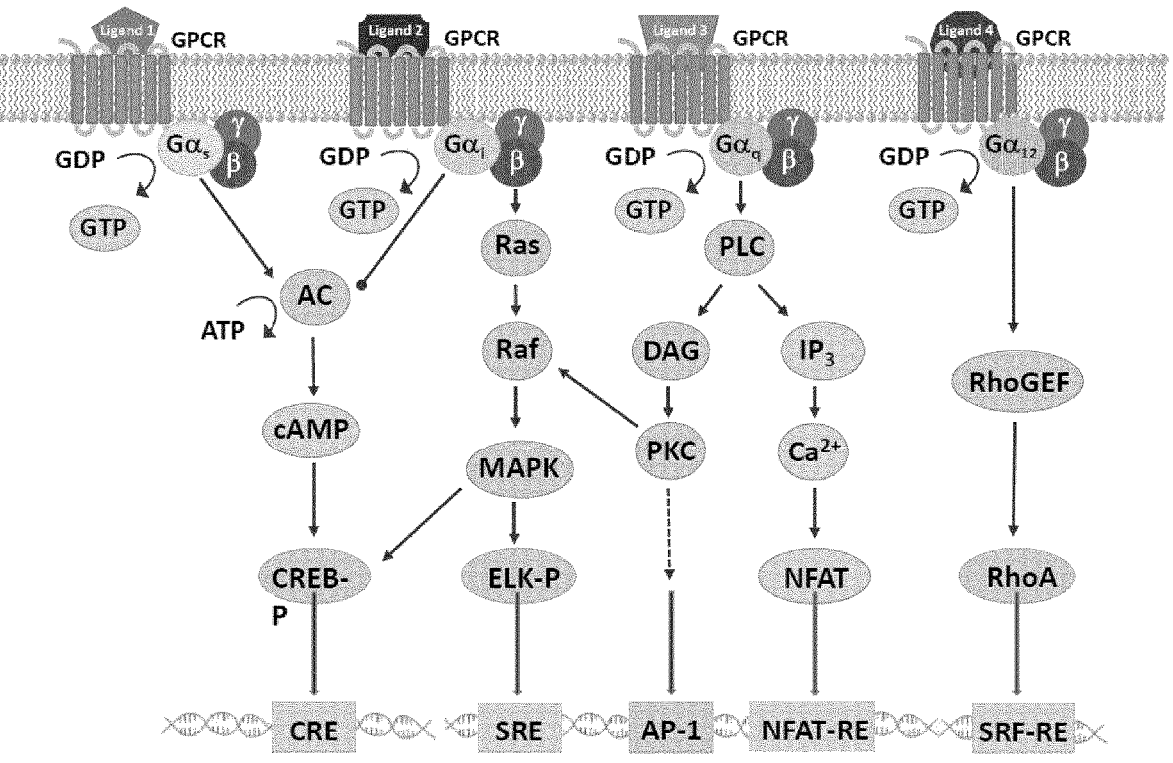
FIG. 2. General scheme for G-protein activation. The G protein signal is transmitted from activated receptor to second messenger molecules by different effectors, which are in turn triggered by the α-subunit as well as the βγ-subunits. The versatility of the triggered effectors depends also on the subunit subtypes: the Gα$_s$ subunit induces the cAMP production after receptor activation regulating the cAMP response element (CRE) transcription factor, while the Gαi inhibits the camp formation. The Gαq subunit induces the increase inositol 1,4,5 triphosphate (IP3) concentration provoking the activation of the two transcription factors: the nuclear factor of activated T cells (NFAT) and the activator protein 1 (AP-1). The Gα12 subunit controls the regulation of the serum response factor (SRF). The subunit Gβγ activation leads to the transcription of the serum response element (SRE) factor. All the elements colored in turquois blue are targeted by existing screening assays.
Figure 3:
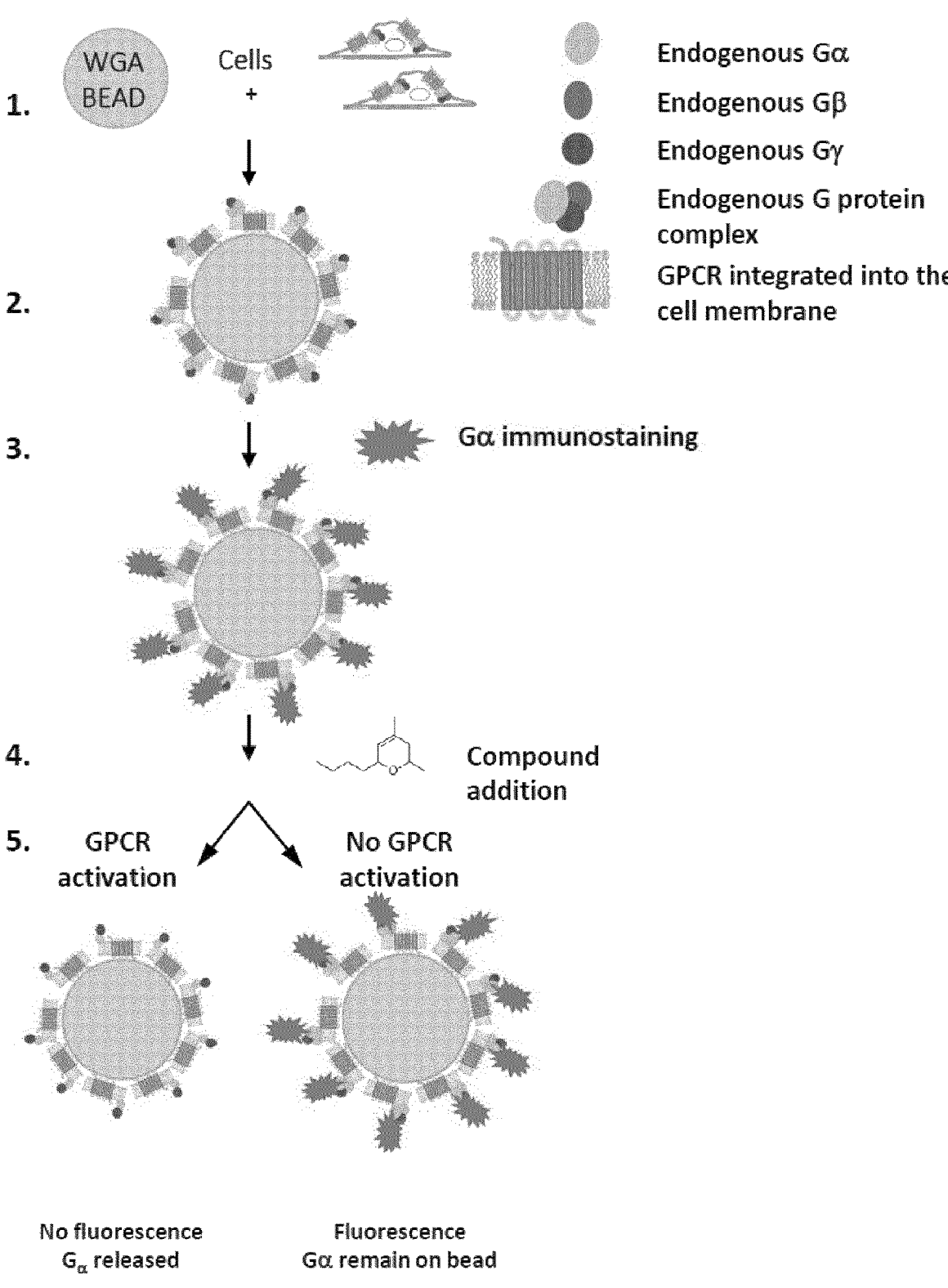
FIG. 3. Schematic representation of the synthetic GPCR screening platform. 1. Mammalian cells expressing endogenous G-proteins and a particular GPCR (heterologous or endogenous) are incubated with micrometer-sized agarose beads which are coated with WGA (wheat germ agglutinin). Cells bind with their surface exposed glycosylation sites to the WGA on the beads. 2. Shaking beads disrupt the adsorbed cells leaving cellular plasma membrane fragments attached to the beads in an inside-out orientation making both intracellular and the extracellular surfaces of the plasma membranes accessible. 3. The Gα-protein subunits of the plasma membranes at the beads are immunostained by first binding an antibody against Gα followed by binding of a fluorescent secondary antibody. This leads to fluorescence labeled Gα-protein subunits. 4. Specific binding of an agonist to a particular GPCR present in the plasma membranes activates the receptor and its heterotrimeric G-proteins and finally induces the release of the Gα-subunits from the heterotrimeric G-protein complexes. 5. This process is accompanied by the release of the fluorescent antibody. The corresponding disappearance of the fluorescence signal from the bead can be followed by fluorescence microscopy or flow cytometry. Alternatively, an increase of the fluorescence signal in the bead surrounding medium can be measured.
Figure 4:
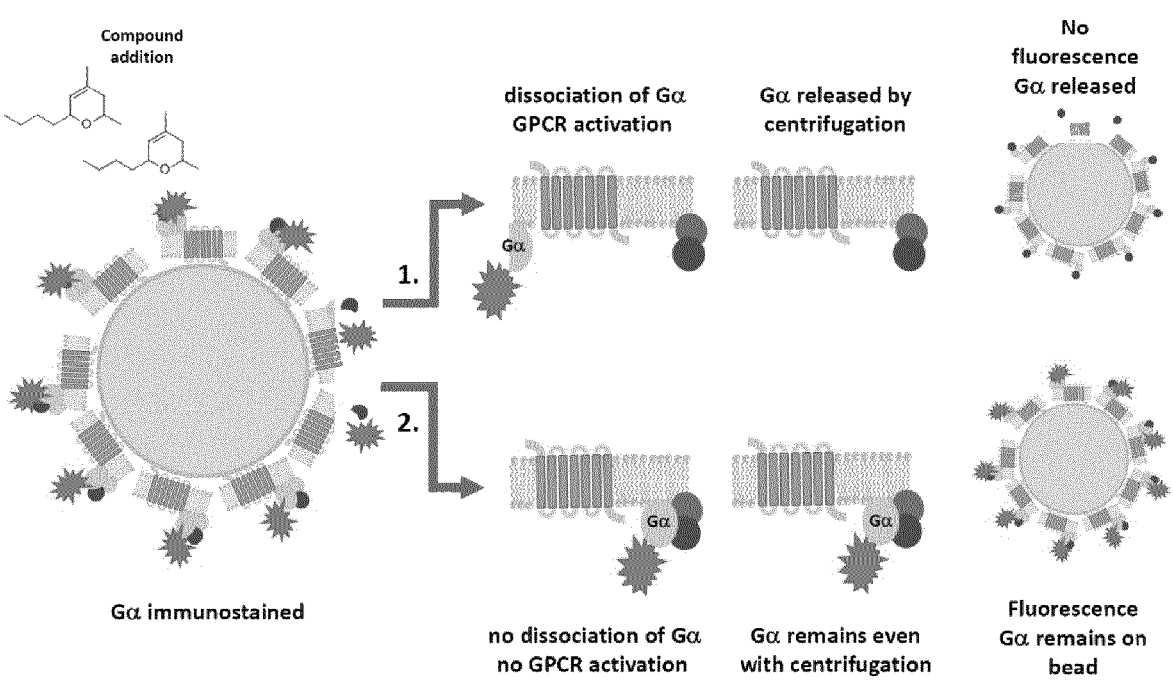
FIG. 4. Detailed scheme of the membranes coated-beads activation. 1. The addition of compound triggers the activation of the GPCR and leads to the dissociation of the Gα subunit from the other subunits and the GPCR. The Gα subunit is released from the membrane by centrifugation and no fluorescence is observed. 2. The addition of compound does not activate the GPCR, the Gα subunit remains associate to the other subunits at the plasma membrane, the fluorescence is observed.
Figure 5:
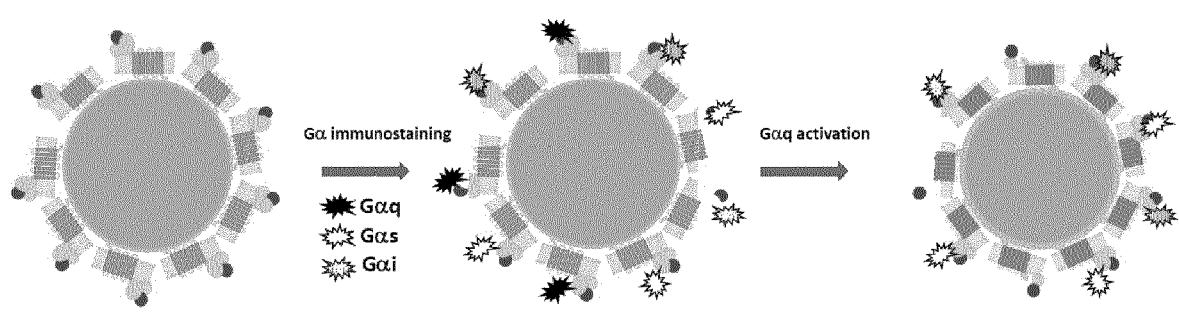
FIG. 5. Multi-labeling of the different Gα subunits. The subunits Gαq, Gαi and Gαs can be labeled at the same time with different fluorophores allowing the specific GPCR-G protein screening in one assay.
Figure 6:
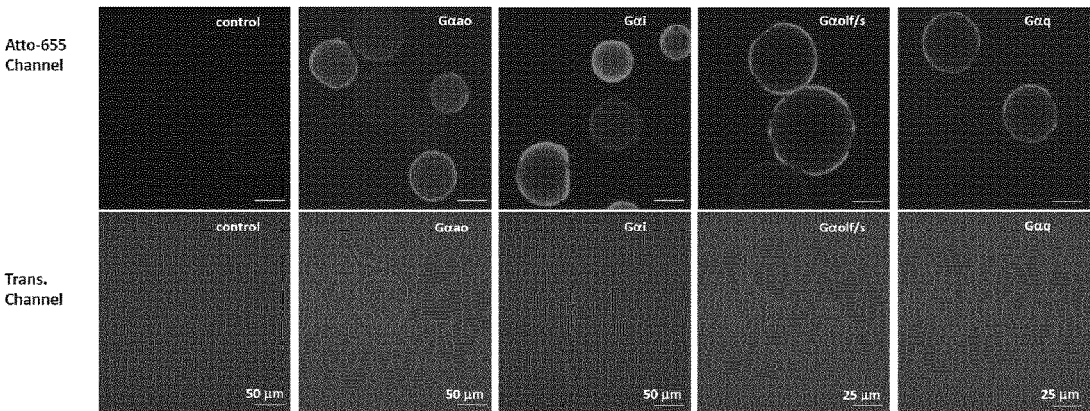
FIG. 6. Confocal microscopy images showing different forms of Gα subunits in plasma membranes transferred from HEK cells to WGA-beads and stained with antibodies specific to either Gαi, Gαs or Gαq labeled with Atto-655. Row A: Fluorescence images. Row B: Transmission images. (Scale bar: 50 μm)
Figure 7:
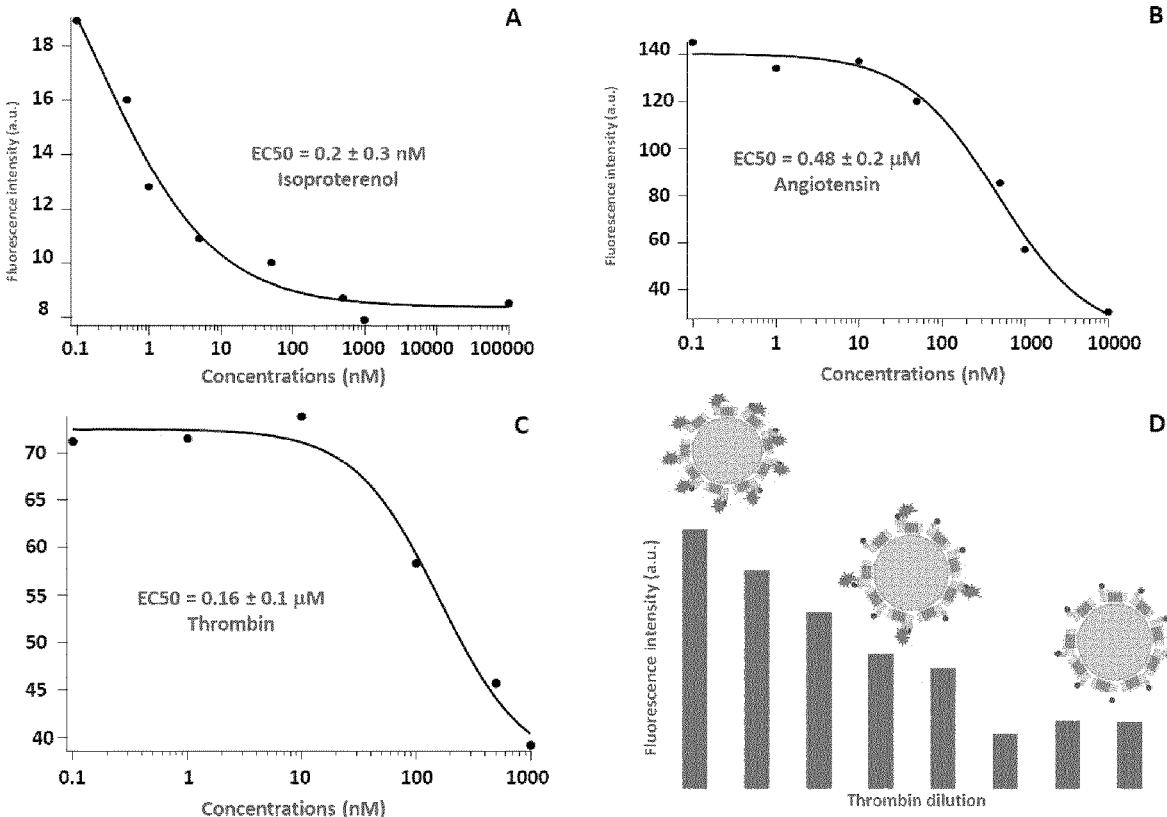
FIG. 7. Dose response curves of GPCR activation in plasma membranes on beads. (A) Plasma membranes (PMs) are transferred from HEK cells to WGA-beads and the endogenous the β2-adrenergic activates the Gαs with different concentrations of isoproterenol. (B) PMs comprising the angiotensin receptor which is activated in a dose-dependent manner by its native agonist angiotensin triggering finally the release of Gαi endogenously present in the PMs of HEK cells (C) PMs comprising the Protease-activated receptor PAR which is activated by different concentrations of thrombin triggering finally the release of Gαq endogenously present in the PMs of HEK cells. (D) Schematic representation of a dose response curve using the immunostained beads method.

The subject matter herein described will be clarified by means of the following description. It is however to be understood that the subject matter described in this specification is not limited to the aspects described herein and depicted in the drawings; to the contrary, the scope of the subject-matter herein described is defined by the claims. Moreover, it is to be understood that the specific conditions or parameters described and/or shown in the following are not limiting of the subject matter herein described, and that the terminology used herein is for the purpose of describing particular aspects by way of example only and is not intended to be limiting.

Unless defined otherwise, technical and scientific terms used herein have the same meaning as commonly understood by one of ordinary skill in the art to which this invention belongs. Further, unless otherwise required by the context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

Non-limiting aspects of the subject-matter of the present disclosure will be described by way of example with reference to the accompanying figures, which are schematic and are not intended to be drawn to scale. For purposes of clarity, not every component is labelled in every figure, nor is every component of each aspect of the invention shown where illustration is not necessary to allow those of ordinary skill in the art to understand the invention.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

In the frame of the present disclosure, the expression "operatively connected" and similar reflects a functional relationship between the several components of the device or a system among them, that is, the term means that the components are correlated in a way to perform a designated function. The "designated function" can change depending on the different components involved in the connection. Likewise, any two components capable of being associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components. A person skilled in the art would easily understand and figure out what are the designated functions of each and every component of the device or the system of the invention, as well as their correlations, on the basis of the present disclosure.

The term "about" particularly in reference to a given quantity, is meant to encompass deviations of plus or minus ten (10) percent (e.g. ±10%). For example, about 5 μm also encompasses 4.5 to 5.5 about 70 μm also encompasses 63 to 77 μm, etc. . . .

By at least one is meant, one or more, two or more, three or more, etc. . . .

A "microfluidic device" is generally speaking any apparatus which is conceived to work with fluids at a micro/nanometer scale. Microfluidics is generally the science that deals with the flow of liquids inside channels of micrometer size. At least one dimension of the channel is of the order of a micrometer or tens of micrometers in order to consider it microfluidics. Microfluidics can be considered both as a science (study of the behavior of fluids in microchannels) and a technology (manufacturing of microfluidics devices for applications such as lab-on-a-chip). These technologies are based on the manipulation of liquid flow through micro-fabricated channels. Actuation of liquid flow is implemented either by external pressure sources, external mechanical pumps, integrated mechanical micropumps, hydrostatic pressures or by combinations of capillary forces and elec-trokinetic mechanisms. In the frame of the present invention, a microfluidic device can be easily adapted to work with fluid volumes spanning from milliliters down to femtoliters, and the dimensions can be adapted accordingly to have channels within the millimeter scale.

As used herein, a "polymeric material" is any material comprising polymers, large molecules (also known as mac-romolecules) composed of many repeated smaller units, or subunits, called monomers, tightly bonded together by cova-lent bonds. Cross-linked polymers have monomers of one long or short chain covalently bonded with monomers of another short or long chain. Cross-linking results in a three-dimensional molecular network; the whole polymer is a giant macromolecule. Another classification of polymers is based on the chemical type of the monomers: homopolymers consist of monomers of the same type, copolymers have different repeating units. Furthermore, depending on the arrangement of the types of monomers in the polymer chain, there are the following classification: the different repeating units are distributed randomly (random copolymer) or there are alternating sequences of the different monomers (alter-nating copolymers) in block copolymers long sequences of one monomer type are followed by long sequences of another type; and graft copolymers consist of a chain made from one type of monomer with branches of another type. Elastomers (also called rubbers) are lightly cross-linked networks while thermosets are densely cross-linked net-works. Rubbers are characterised by the property of high elasticity, i.e. elastic behaviour at high stresses and strains. Polymers can be diluted in a variety of solvents (usually organic but there are a few polymers called polyelectrolytes which are water soluble). A sufficiently dense polymer solution can be crosslinked to form a polymer gel, including a hydrogel or a cryogel, which is a soft solid. Polymer materials may also be formed by blending two or more polymers into physical mixtures.

The term "hydrogel" refers to a gel in which the swelling agent is water. A hydrogel is a macromolecular polymer gel constructed of a network of cross-linked polymer chains. It is synthesized from hydrophilic monomers, sometimes found as a colloidal gel in which water is the dispersion medium. Hydrogels are highly absorbent (they can contain over 90% water) natural or synthetic polymeric networks. As a result of their characteristics, hydrogels develop typical firm yet elastic mechanical properties.

As will be detailed later on, polymeric materials can be used in some embodiments to constitute beads according to the invention. Some examples of suitable polymers include, without limitation, natural polymers, such as polysaccha-rides (cellulose, modified cellulose, agarose, alginate, starch, modified starch, chitosan and many others), co-polymers of polysaccharides, polypeptides (silk, collagen, gelatin and many others), amelogenin, proteoglycans and/or glycosami-noglycanes such as hyaluronic acid, chondroitinsulfate, der-matansulfate, heparansulfate, heparine or keratansulfate;

additional polymers are synthetic polymers such as sili-cones, polyurethanes, poly-olefins, acrylates, polyesters, polyamides, polyimides including alkyds, epoxies, pheno-lics (e.g., Bakelite), polyimides, formaldehyde resins (e.g., urea formaldehyde or melamine formaldehyde), polyester thermosets, unsaturated polyesters, polyurethane, bis-male-imides (BMI), silicone materials such as polydimethylsi-loxane (PDMS) and any combination thereof. Further suit-able materials according to the present invention may comprise one or more compounds selected from a non-exhaustive list comprising poly(lactic-co-glycolic acid), lac-tide and glycolide polymers, caprolactone polymers, hydroxybutyric acid, polyanhydrides, polyesters, polyphos-phazenes, polyphosphoesters and poly(glycerol sebacate acrylate), polypropylene, polypropylenoxide or their deriva-tives, polymethylenoxide or its derivatives, polyethylene or its derivatives such as polyethylene glycole (PEG), polyeth-ylenoxide or their derivatives, polyacrylate or its derivatives, poly(vinyl alcohol) (PVA) and copolymers, poly(vinylpyr-rolidone) (PVP), Poly(N-isopropylacrylamide) (PNIPAM), Poly(acrylic acid) (PAA) and combinations thereof. CHECK SUITABILITY As used herein, "cell surface receptor" refers to molecules that occur on the surface of cells, interact with the extracel-lular environment, and transmit or transduce the information regarding the environment intracellularly in a manner that ultimately modulates transcription of specific promoters, resulting in transcription of specific genes. "Orphan recep-tors" is a designation given to a receptors for which no specific natural ligand has been described.

Agonists and antagonists are "receptor effector(s)", mol-ecules that modulate signal transduction via a receptor. Receptor effector molecules are capable of binding to the receptor, though not necessarily at the binding site of the natural ligand. Receptor effectors can modulate signal trans-duction when used alone, i.e. can be surrogate ligands, or can alter signal transduction in the presence of the natural ligand, either to enhance or inhibit signaling by the natural ligand. For example, "antagonists" are molecules that block or decrease the signal transduction activity of receptor, e.g., they can competitively, noncompetitively, and/or allosteri-cally inhibit signal transduction from the receptor, whereas "agonists" potentiate, induce or otherwise enhance the sig-nal transduction activity of a receptor. The terms "receptor activator" and "surrogate ligand" refer to an agonist which induces signal transduction from a receptor. The term "modulation of a signal transduction activity of a receptor protein" in its various grammatical forms, as used herein, designates induction and/or potentiation, as well as inhibi-tion of one or more signal transduction pathways down-stream of a receptor.

According to a main object of the present disclosure, it is provided herein a method for determining the presence of a molecule coupled to the cytoplasmic side of a cellular membrane, comprising the steps of:

a) providing a plurality of micrometric beads, each located in a trap of a multi-trap microfluidic device;

b) loading a plurality of cells into said microfluidic device, in a way that at least one cell adhere to at least one micrometric bead;

c) breaking the bead-attached cells to expose cellular plasma membrane fragments on the beads in an inside-out orientation;

d) loading into said microfluidic device a labelling com-pound specific for a molecule coupled to the cytoplasmic side of a cellular membrane; and e) detecting a signal associated with the presence of said labelling compound, wherein said signal is indicative of the presence of said molecule coupled to the cytoplasmic side of a cellular membrane.

By the use of the method according to the invention, the presence of medium-sized or macro-molecules such as a protein, a multi-protein complexes and/or a lipid molecule can be determined in a rapid and precise manner by visual means. Typically, the molecules coupled to the cytoplasmic side of a cellular plasma membrane are anchored thereto, typically via covalent bonds, and/or are coupled to the cytoplasmic side of transmembrane proteins or complexes.

Additionally, the method according to the invention can be used to test molecules, such as small molecules, oligo-peptides or polypeptides, which induce a receptor signalling activity. As previously outlined, and as will be further detailed along the present disclosure, the methods according to this invention have been particularly, but not exclusively, implemented to optimize current GPCR-related screening methods. According to a main object of the present disclosure, therefore, a "molecule coupled to the cytoplasmic side of a cellular membrane" is selected from a non-limiting list comprising a GαGDP-βγ heterotrimeric G protein, a GαGTP subunit of a G protein, an arrestin protein, an arrestin bound with at least one of a RAF protein, a MEK protein or an ERK proteins, or a GPCR kinase (GRK).

The present assay is useful for identifying polypeptides that interact with any receptor protein whose activity ulti-mately induces a signal transduction cascade in the host cell which can be exploited to produce a detectable signal. In particular, the method can be used to test functional ligand-receptor or ligand-ion channel interactions for cell surface-localized receptors and channels, among others. The present assay can be used to identify effectors of, for example, G protein-coupled receptors, receptor tyrosine kinases, cyto-kine receptors, and ion channels, as well as steroid hormone receptors. In some embodiments, the method described herein is used for identifying ligands for "orphan receptors" for which no ligand is known.

Accordingly, the present invention provides a convenient, rapid and effective format for discovering bioactive com-pounds which can be useful to modulate cellular function, as well as to understand the pharmacology of compounds that specifically interact with, and modulate the activity of, cellular receptors or ion channels. Moreover, the subject assay is particularly amenable to identifying ligands, natural or artificial, for orphan receptors.

In one embodiment, a test compound is assayed for its ability to antagonize, e.g., inhibit or block the activity of a receptor (ability to act as an "antagonist"). Additionally or alternatively, the assay can test for the ability of a compound to act as an "agonist", i.e. to induce activation of receptor signalling pathways, e.g., such as by mimicking a ligand for the receptor, as well as agents which potentiate the sensi-tivity of the receptor to a ligand, e.g., lower the concentra-tions of ligand required to induce a particular level of receptor-dependent signalling.

The receptor protein can be any receptor which interacts with an extracellular molecule (i.e. hormone, growth factor, peptide) to modulate a signal in the cell. As a way of example, the receptor can be a cell surface receptor. In some embodiments, the receptor can be a receptor tyrosine kinase, e.g., an EPH receptor; an ion channel; a cytokine receptor; a multisubunit immune recognition receptor, a chemokine receptor; a growth factor receptor, or a G-protein coupled receptor, such as a chemoattractant peptide receptor, a neuropeptide receptor, a light receptor, a neurotransmitter receptor, or a polypeptide hormone receptor.

Preferred G protein coupled receptors include, e.g., α1A-adrenergic receptor, al B-adrenergic receptor, α2-adrenergic receptor, α2B-adrenergic receptor, β1-adrenergic receptor, β2-adrenergic receptor, β3-adrenergic receptor, m1 acetyl-choline receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1 d receptor, 5HT1d-like receptor, 5HT1 d beta recep-tor, substance K (neurokinin A) receptor, fMLP receptor, fMLP-like receptor, angiotensin II type 1 receptor, endothe-lin ETA receptor, endothelin ETB receptor, thrombin recep-tor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leu-tropin (LH/HCG) receptor, thyroid stimulating hormone (TSH) receptor, thromboxane A2 receptor, platelet-activat-ing factor (PAF) receptor, C5a anaphylatoxin receptor, Inter-leukin 8 (IL-8) IL-8RA, IL-8RB, Delta Opioid receptor, Kappa Opioid receptor, mip-1/RANTES receptor, Rhodop-sin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor receptor, antidiuretic hormone receptor, glucagon receptor, and adre-nocorticotropic hormone II receptor.

With respect to the target receptor, it may be endog-enously expressed by the host cell, or it may be expressed from a heterologous gene that has been introduced into the cell. Methods for introducing heterologous DNA into eukaryotic cells are of course well known in the art and any such method may be used. In addition, DNA encoding various receptor proteins is known to those of skill in the art or it may be cloned by any method known to those of skill in the art. In certain embodiments, such as when an exog-enous receptor is expressed, it may be desirable to inacti-vate, such as by deletion, a homologous receptor present in the cell.

Suitable host cells for generating the subject assay include prokaryotes, yeast, or higher eukaryotic cells, especially mammalian cells. Prokaryotes include gram negative or gram positive organisms. Examples of suitable mammalian host cell lines include without limitations 3T3, Chinese hamster ovary (CHO), HeLa and BHK cell lines, as well as primary cells.

As anticipated, the method of the invention is imple-mented in a microfluidic setting by the use of a microfluidic device or chip. Said chip is designed and configured to comprise, in preferred embodiments, a plurality of so-called traps to accommodate micrometric beads, acting as "baits" for the cells to be analysed. Particularly, the chip can comprise arrays of traps located in rows and/columns to maximize the active surface of analysis, i.e. the maximum number of cells under investigation.

The materials typically used for the production of the microfluidic device, including valves whenever present, are soft materials, elastomers such as poly(dimethyl siloxane) (PDMS) or even hard materials such as thermoplasts, ther-mosets or glass. Using a transparent or translucent material advantageously allows to visually check the entire process.

Suitable ways of manufacturing the device are known in the art and can include etching, lithography, 3D printing, hot embossing and so forth.

The microfluidic design is based on hydrodynamic trapping of particles, a passive mechanism that uses physical constriction (traps) along flow lines to immobilize object of specific sizes at specific locations. Arrays of such traps are tailored to the method of the present invention, and in particular to the adequate bead size enabling single bead trapping and preventing bead clogging. The overall chip is composed of five main parts.

Figure 9:
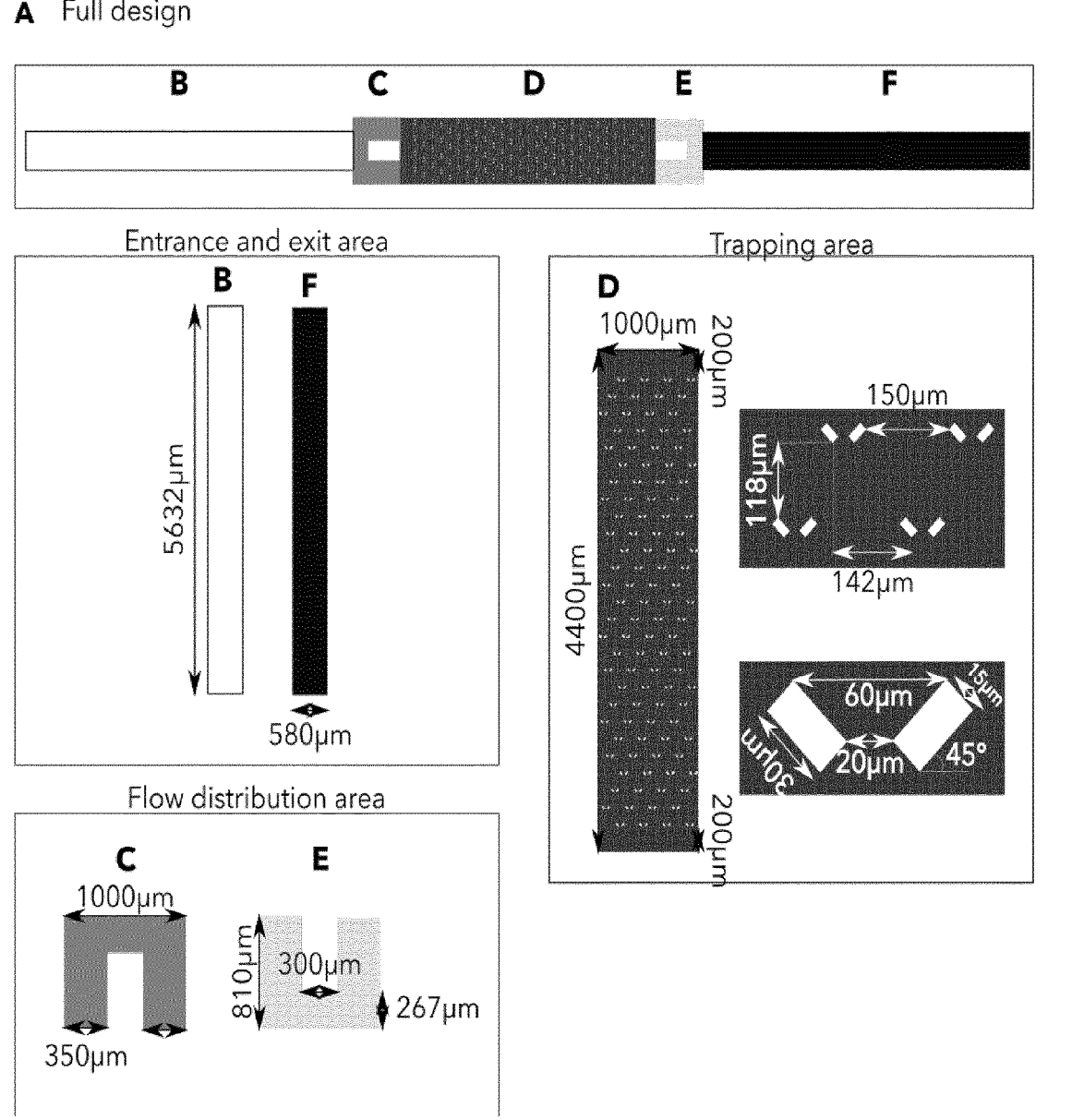
FIG. 9. Schematic of the chip design. (A) Full chip design composed of 5 fluidic modules, the entrance area (B), the homogenous widening flow distribution area (C), the main trapping area (D), the homogenous flow narrowing distribution area (E) and the exit area (F). Each specific module dimensions are described under the entrance and exit area ((B) and (F)), flow distribution areas ((C) and (E)) and trapping area (D) with more detailed information on the trap line arrangements and the trap dimensions. The dimensions presented here are purely indicative and similar performances could be achieved with different chip dimensions tailored to the cell, bead sizes and amounts.

The entry access channel (FIG. 9B) enables the laminar flow to establish correctly in the microfluidic device. The channel is at this position to link the entrance point through an opening for the particles and reagents to the functional part of the device (trapping area).

A flow distribution area (FIG. 9C) allows to fully and homogeneously distribute the flow along the entire channel width to have a uniform concentration distribution of particles (beads/cells) and reagents over the entire channel width. The design is optimized to decrease the effect of the parabolic flow profile occurring in microfluidic devices leading to higher flow speed at the centre of the channel and lower flow speed on the channel walls. This is achieved by splitting the flow from the entrance channel into two distinct channels separated by a solid pillar.

The main trapping portion (FIG. 9D) is the core functional part of the device. A buffer zone of e.g. 200 µm long at the entrance and exit of the chamber is framing the trapping region. The aim is to enable homogenous particle spreading in the reaction chamber and increase the trapping efficiency for the first sets of traps. The trapping region is composed of trap lines perpendicular to the flow direction (spaced to prevent bead doublets clogging) containing several traps (spaced to prevent bead doublets clogging). The number of traps can easily be tailored to the need of the experiments and the desired statistical power. Each trap line is shifted to prevent previous traps to shield particles from going in the following traps. The aim is to shift the flow streamlines going from the first trap lines to the subsequent ones, and hence enhance the trapping efficiency of all traps in the device independently of their position related to the entrance of the chamber.

The traps are composed of two rectangular pillar subunits rotated of 45°, to create a V shape accommodating the beads. Each subunit is spaced 20 µm at the narrowest end and 62 µm at the widest end of the V. These dimensions are used to accommodate trapping of e.g. agarose beads ranging from 20 µm to 70 µm and preventing any double trapping of beads in each trap location.

A subsequent flow narrowing area (FIG. 9E) aims to homogenously re-concentrate the flow. The design is a mirrored design from the flow distribution area. These dimensions enable a narrowing of the chip up to the exit channel (FIG. 9F), linking the exit point through an opening in the chip for release of particles and reagents.

The microfluidic chip can be fluidically connected to one or more reservoir(s), each containing a fluid sample such as for instance a buffer, a culture medium (possibly loaded with cells) and the like. Whenever needed, reservoirs are operably connectable with a pressure source adapted to apply a pressure thereon. The pressure applied can be a positive pressure, i.e. when the applied pressure increases the internal reservoir fluid pressure, or a negative pressure, i.e. when the applied pressure diminishes the internal chamber or reservoir fluid pressure, as in case of a suction. A means to apply a pressure will usually be coupled with a reservoir either directly or indirectly (via e.g. a connection tube). Suitable means of altering the pressure within the device are external or integrated pumps or micropumps, combinations of capillary forces and electrokinetic mechanisms, hydrostatic pressure or simply a syringe. As will be evident for a skilled in the art, for what said above, the invention is intended to cover also a system comprising a microfluidic device as defined above and pressure means operably connected to a reservoir adapted to generate a pressure within said reservoir, in a way as to let flow the reservoir's content or at least a part of it into the microfluidic chip.

With regards to the beads used in the frame of the present method, these are substantially composed of one or more polymeric material(s), composite materials such as polymeric ones mixed with metal particles or the likes, or even inert materials such as silica glass. Advantageously, the beads have a diameter comprised between 5 and 70 such as between 20 and 70 and are in some embodiments at least partially coated on their surface with a molecule capable of interacting and binding to an extracellular cell-membrane molecule, such as a lectin. The features of the so-composed beads, and particularly the specific diameter size range of the beads, are expedient to enhance the efficiency of the interaction with the cells under analysis and reduce the loss of material in the implementation of the method.

According to a first step of the method at stake, the beads are loaded or otherwise provided inside the microfluidic chip in such a way that each bead is located in a trap of a multi-trap microfluidic device. The traps are specifically designed to host one single bead to avoid any artefacts, and in a way to expose the maximum surface possible to augment the available contact surface.

In a second method step, a plurality of cells to be tested are loaded into said microfluidic device, in a way that at least one cell adhere to at least one micrometric bead. Typically, the adhesion is due to the interaction between the glycosylated molecules present in the cell membrane surface with the coating substrate present on the surface of the beads, which can be for instance wheat germ agglutinin (WGA).

In a third step, the bead-attached cells are broken, such as by lysis, shear stress or combinations of the foregoing, through a buffer as e.g. a lysis buffer injected into the chip, so to expose cellular plasma membrane fragments on the beads in an inside-out orientation. Gentle shaking, pressure means or otherwise mechanical friction can be implemented to enhance the buffer action.

During a fourth step, the microfluidic device is loaded with a labelling compound specific for a molecule of interest coupled to the cytoplasmic side of a cellular membrane. Advantageously, the labelling compound can be a fluorescent compound detectable through e.g. a fluorescence microscope such as an antibody specific for the molecule(s) of interest coupled with a fluorescent dye or molecule, radiopaque or radioactive particles or agents such as metallic nanoparticles detectable through e.g. radiographic imaging means, biotin-streptavidin interaction revealable through chemiluminescence and the like.

In a fifth step, a signal associated with the presence of said labelling compound is detected. Said signal is indicative of the presence of the molecule of interest coupled to the cytoplasmic side of a cellular membrane. Means for detecting a labelling compound can include, as anticipated, fluorescence microscopy, radiographic imaging means, chemiluminescence techniques and so forth, techniques which are well known to a person skilled in the relevant art. CHECK ALL THIS PART AND IMPLEMENT IF NEEDED.

In a particular embodiment of the invention, the molecule coupled to the cytoplasmic side of a cellular membrane is a GαGTP subunit of a G protein, an arrestin protein or a labelled GTP molecule, further comprising a step of contacting the cellular plasma membrane fragments on the beads with a molecule to be tested for an activity on a G protein-coupled receptor wherein a detected signal associated with the removal of a loaded labelling compound specific for a molecule coupled to the cytoplasmic side of a cellular membrane is indicative of the presence of said GαGTP subunit of a G protein, and therefore a lack of activity of the tested molecule on a G protein-coupled receptor or wherein a detected signal associated with the removal of a loaded labelling compound specific for a molecule coupled to the cytoplasmic side of a cellular membrane is indicative of the presence of an arrestin protein or GTP labelled molecule, and therefore the presence of an activity of the tested molecule on a G protein-coupled receptor.

In this embodiment, a particular GPCR is heterologously or endogenously expressed in mammalian cells which heterologously or endogenously express G-proteins or arrestin proteins suitable to couple to the before-mentioned GPCR. Suitable mammalian cells can be cells such as HEK cells or CHO cells expressing particular GPCRs and G proteins/arrestin. Alternatively, especially for biomedical diagnostics, primary cells such as tumour cells from patients' samples could be used.

Figure 8:
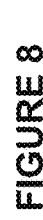
FIG. 8. Schematic representation of the method. 1) The wheat germ agglutinin (WGA) coated beads are loaded on a microfluidic device containing multiple designed traps. The beads are then confined at specific locations. 2) When all the traps are filled, cells are introduced into the chip. The flow allows the cells to bind to the WGA bead via their glycosylated cell surface. After few minutes, the bead is completely covered of mammalian cells. 3) To obtain membrane-coated beads a lysis buffer is applied for a certain time. 4) The Gα subunits fully accessible are labeled with a specific antibody and then with a fluorescent antibody. 5) Addition of agonists to the bulk will eventually bind to and activate the targeted GPCR in the bead attached membrane. The activation is detected with the loss of fluorescence.

All the steps are implemented in an optimized multi-trap microfluidic chip, typically consisting of a single layer of PDMS. First, beads such as agarose beads coated with wheat germ agglutinin (WGA) are filtered to obtain a plurality thereof having an average diameter size comprised between about 5 μm and about 70 μm, preferably between about 20 μm and about 70 μm, corresponding to an optimized diameter size for an efficient and successful cell coating. Then, as schematically depicted in FIG. 8: 1) the beads are introduced in the chip and intercepted by the traps designed according to the optimized diameter size beads.

The cells to be tested are then loaded in the chip in a buffer solution (for instance, a culture medium) and incubated with the beads. During this step, the cells bind via their glycosylated cell surface proteins to the WGA on the beads. The flow of the solution is stopped when the cells overlay completely the WGA beads. Subsequently, the chip is filled with a lysis buffer that breaks open the bead coated-cells leaving cellular plasma membrane fragments on the beads in an inside-out orientation. In this configuration, both the cytoplasmic side as well as the extracellular side of the plasma membrane fragments are fully accessible. The plasma membranes derived from the before-mentioned mammalian cells comprise the heterologous or endogenous GPCRs and a corresponding heterotrimeric G-proteins forming fully functional GPCR/G-protein signalling complexes and/or GPCR/arrestin complexes.

A Gα subunit or an arrestin is then e.g. fluorescently labelled using two steps immunostaining. The chip is finally filled with special activation buffer containing a receptor effector to be tested for an activity on a G protein-coupled receptor, such as an agonist of a GPCR that eventually binds to and activates the particular GPCR under examination on the bead-attached membrane. The agonist-activated GPCR will in turn interact with the GTP-bound form of the G-protein and in turn induce the dissociation of the heterotrimeric G protein, releasing the Gα subunit into the medium while the Gβγ subunits remain at the plasma membrane.

As the Gα subunit is fluorescently labelled, the corresponding fluorescence signal is, during the G protein dissociation process, also released from the plasma membrane on the beads to the medium, so that it will be no longer detectable. To the opposite, a detected signal associated with the removal of a fluorescent antibody is indicative of the presence of said GαGTP subunit of a G protein, and therefore a lack of activity of the tested molecule on a G protein-coupled receptor. In the outline of the assay platform, the Gα subunit is fluorescently labelled via antibodies (a specific first antibody binds to the Gα and a fluorescently labelled secondary antibody binds selectively to the first antibody) which remain closely attached during the entire GPCR activation/signalling process to the Gα subunit. Alternatively, a fluorescently labelled specific antibody (IgG type or single chain antibody/nanobody) could be used in order to avoid the use of a secondary antibody. The change of fluorescence signal on the beads and/or in the bead surrounding medium created by activation of GPCR signalling is monitored time-resolved by a fluorescence microscope.

To the contrary, a detected fluorescence signal associated with the removal of a specific labelling compound, such as a fluorescent antibody, is indicative of the presence of an arrestin protein or GTP labelled molecule, and therefore the presence of an activity of the tested molecule (receptor effector) on a G protein-coupled receptor.

The configuration of this assay platform shows a number of distinct advantages over present solutions known in the art: 1) a wide variety of native GPCRs (genetically and chemically unmodified) can be investigated only limited by their capability to express either heterologously or endogenously in the corresponding cells to be used for investigation; 2) the use of a specific antibody against a particular Gα subunit either heterologously or endogenously present in the cell allows to determine the direct activation of the native G-protein involved in the particular GPCR activation process. Activation of different G protein pathways can be easily distinguished by using a distinct antibody against the particular Gα subunit allowing the screening of all the Gα subunits at the same time; 3) as the activation of the GPCR is detected at an early stage of the signalling cascade, crosstalk by downstream elements is prevented; 4) the membranes attached on beads deliver a very sensitive and robust fluorescence readout of G-protein dissociation upon agonist induced GPCR activation. Kinetic and dose-dependent activity profiles of compounds can be established. The bead-based platform allows extreme miniaturization (microliter sample volumes, consumption of few or even single-cells) in a high throughput format; 5) it is possible to extend the assay format by labelling the corresponding native GPCR with a fluorescent antibody which can be fluorescently distinguished from the antibody at the G protein. In this configuration it is possible to determine the association and kinetic constants of the interaction between the GPCR and its G protein and how it is changed upon agonist induced activation of the signalling; 6) beads comprising immobilized plasma membranes can be stored for several months at −80° C. without loss of their GPCR signalling capabilities.

As it will be evident for a person skilled in the art, another object of the present invention relates to a kit comprising at least a multi-trap microfluidic device, a plurality of polymeric beads and instructions to perform a method according to the present disclosure. The kit according to the invention may optionally further comprise a labelling compound specific for a molecule coupled to the cytoplasmic side of a cellular membrane, particularly an antibody or any deriva-tive thereof (such as e.g. multivalent antibodies, multispecific antibodies, scFvs, bivalent or trivalent scFvs, triabodies, minibodies, nanobodies, diabodies) and/or functional fragment thereof (e.g. an Fv region, a Fab/F(ab')/F(ab')2 region or fusion proteins thereof) coupled with a fluorescent, radioactive or radiopaque compound; a labelling compound for a biotin/streptavidin chemiluminescent assay and the like. The molecule coupled to the cytoplasmic side of a cellular membrane may preferably be a labelled GTP molecule, a GαGDP-βγ heterotrimeric G protein, a GαGTP subunit of a G protein, an arrestin protein, an arrestin bound with at least one of a RAF protein, a MEK protein or an ERK proteins, a GPCR kinase or combinations thereof.

The beads comprised in the kit include polymeric beads or glass silica beads, among others, and there are preferably coated, at least partly, with a binding molecule capable of interacting and binding to an extracellular cell-membrane molecule. Said binding molecule can be for instance WGA. Alternatively, the kit may further comprise a compound, such as for instance WGA, to coat the beads. The beads comprised in the kit have an average diameter comprised between about 5 and about 70 such as between about 20 and about 70 which is the beads' size range that has proved to be the most efficient in terms of cell membrane coupling.

EXAMPLES

Microfabrication

The microfluidic device was fabricated in polydimethylsiloxane (PDMS). Silicon (Si) masters were patterned with a soft photolithography step followed by a silicon etching step. The Si wafer was primed with hexamethyldisilizane (HMDS) then AZ1512 HS (AZ 1500 series, MicroChemicals) positive photoresist was spun at 3000 rpm for 30-40 sec to yield feature heights of 2 μm (ACS200 Gen3, Suss MicroTec) with a post-exposure bake for 1:30 min at 112° C. The wafers were exposed to ultraviolet light through direct writing (VPG200 Photoresist Laser writer, Heidelberg) to pattern the channels. After resist development the Si was etched to a final height of 20 μm using a Bosch process (AMS 200SE, Adixen). The photoresist was then stripped with 5 min Oxygen plasma at 500 W. The final Si mold (Table 5) was silanized at room temperature overnight using Trichloro(1H,1H,2H,2H-perfluorooctyl)silane (PFOTS, Sigma-Aldrich).

Devices were made by mixing curing agent and PDMS polymer (PDMS 184 Sylgard, Dow Corning) at a ratio of 1:10 (wt/wt). The mixture of PDMS was then mixed and degassed in a vacuum chamber for 10 min. The polymer was then poured on the masters and degassed again prior to curing for at least 4h at 80° C.

After PDMS curing the masters were removed. The patterned PDMS slab was then cut out into individual chips and inlets/outlets were punched with a biopsy puncher of 750 μm outer diameter. The PDMS channels were cleaned using frosted tape and then bonded to glass microscope coverslips (24×36 mm, #1,5) with oxygen plasma at 530 mTorr, 29 W for 45 sec.

Bead Suspension Procedure

A suspension of wheat germ agglutinin (WGA) coated-beads was washed first in 5 ml water and then in 5 ml PBS without calcium and magnesium complemented with 1 mM of EDTA. The WGA coated-beads were filtered with a 70 μm strainer (Miltenyi Biotec, USA), resuspended in cold PBSE and kept in ice before experiment.

Cell Suspension Procedure

HEK cells were detached using trypsin-EDTA (GIBCO) for 2 min at 37° C., resuspended in DMEM 10% FBS and centrifugated at 180 g for 2 min. The cell pellet was diluted in PBS complemented with 1 mM of EDTA and filtered with a 40 μm cell strainer (Falcon), before being placed in a 15 mL Falcon tube. The final cell concentration before injection in the microfluidic device was $1 \times 10^6$ cells/ml. Cells were kept on ice before the experiment to prevent receptors internalization.

Buffers and Solutions

To lyse the cells on the beads, a solution (lysis buffer) of 150 mM NaCl (Sigma, Switzerland), 50 mM of Tris-HCl ( ), 5 mM EDTA and 1% of Tween 100 and complemented with protease inhibitors (Roche, Switzerland) has been prepared. The fluorescent GTPγS activation buffer is constituted of 100 mM NaCl, 5 mM MgCl2, 20 mM HEPES, 0.5 mM EDTA and 100 nM to 100 μM of guanine 5'-diphosphate (GDP) (Sigma, Switzerland), the pH has been adjusted at 7.4. The immunostaining activation buffer was prepared with 100 mM NaCl, 50 mM Tris-HCl 10 mM MgCl2, 1 mM EGTA, pH 7.4 supplemented with 5 nM to 100 μM of GDP and 5 nM to 100 μM GTPγS.

Bodipy-TR GTPγS Assay 50 units of Thrombin diluted in fluorescent GTPγS activation buffer has been introduced into the chip containing the cell membrane coated beads already trapped. Then the chip is filled with 10 nM to 10 μM of Bodipy-TR GTP☐S (Fisher scientific, England) in fluorescent GTPγS activation buffer. The increase of fluorescence on the beads was measured with a confocal microscope equipped with a with a 20× dry objective or 40× water immersion objective.

G Protein Immunostaining Assay

The cell membrane coated beads chip was filled with a primary antibody against the a subunits of Gs, Gi or Gq at a dilution comprises between 1:10 and 1:200 in the immunostaining activation buffer. After washing the chip with the washing buffer the cell membrane coated beads were incubated with the secondary antibody (anti-mouse IgG ATTO-633 or anti-rabbit IgG ATTO-655 (both from Sigma-Aldrich, Switzerland). The chip was washed and 1 μM of isoproterenol was added into the chip. The decrease of fluorescence on the beads was measured with a confocal microscope equipped with a 20×dry objective or 40×water immersion objective.

Experimental Setup

The brightfield bead trapping and cell coating steps of the experiments were performed with a Nikon Eclipse TE 300 inverted microscope, at a 20×objective and with a UI3060 camera (IDS). The camera was controlled with the UEye Cockpit software acquiring at 100 frames per second (FPS).

The chips were then placed under hydrostatic flow of buffer (20 μL of buffer was added at the inlet to maintain the beads trapped) on ice or in the fridge (4° C.) until activation experiments. This is a very interesting capability of the system as it enables a decoupling of the cell coating on beads and the activation of the receptor experiment. Hence opening new opportunities of storage of material and subsequent re-analysis or complementary analysis of samples.

The fluorescence GPCR activation experiments were performed on a LSM510 laser scanning microscope (Zeiss) equipped with 20× dry objective. The cell movies were acquired at a frame rate of 1.27 FPS.

An AFM LSPone syringe pump equipped with a 6 entry valves and a syringe size of 1 mL was used to flow the sequential reagents in the device. A Polytetrafluoroethylene (PTFE, IDEX 1569) tubing was used to connect the syringe pump to the microfluidic device and to containers of GTPγS and ligand, while Fluoropolymer (FEP, IDEX 1522) tubing was used to connect the syringe pump to the containers of the lysis buffer, the wash buffer (PBSE), beads and cells. The PTFE tubing is also used at the outlet of the microfluidic device and ends up in a waste reservoir placed below the chip height (to prevent any backflow due to hydrostatic pressure). The pump and tubing were washed with Bleach (14%), followed by EtOH and deionized water, prior and following each set of experiments. They were primed with the appropriate reagents prior to the experiment (to prevent any dead volume and remaining traces of washing agents). If any bubble appeared during washes or pump priming on the piston, isopropanol was flushed in the syringe and removed. The bead and cell movies were analysed using FIJIb software.

Operation Procedure

The chip was manually primed with deionized water using a syringe to remove bubbles. The chip was then connected to the syringe pump with the following valve configuration: 1—Wash buffer, 2—Ø, 3—Lysis buffer, 4—Bead suspension, 5—Microfluidic chip, 6—Cell suspension. Then the bead suspension is flushed in the device at a speed ranging from 100 μL/min to 1 mL/min, the speed used is the highest in the procedure as the beads can withstand high shear stress without deformation. This high flow enables a fast and efficient bead trapping while decreasing the clogging probability. Cells are then pushed through the chip at a lower flowrate between 50 μL/min and 100 μL/min, this flow combines the right drag force to prevent cell sedimentation while maximising the cell coating on beads without destroying the cells. Remaining unattached cells are then washed away with buffer at the same flowrate. The lysis buffer needs to be aspirated at low flowrate in the syringe of the pump to prevent bubble formation due to the presence of surfactant. It is then dispensed at higher flowrate than the one for the cell suspension (up to 200 μL/min) to combine the effect of shear stress and lysis reagents. A washing step is then done at the same speed to remove cell filaments generated during cell lysis. These first steps enable to generate a microfluidic chip filled with beads trapped at specific locations covered with cell membrane.

The chip can then be either detached from the syringe pump or continued to be used for activation experiment. In the first case hydrostatic pressure is applied at the inlet and then stored on ice up to 3 h before activation experiment. Activation experiments either consisted in GTPγS or G protein immunostaining.

For GTPγS experiments the chip was then connected to the syringe pump with the following configuration: 1—Activation buffer, 2—Ligand, 3—Ø, 4—GTPγS-TR, 5—Microfluidic chip, 6—Wash buffer. First the activation buffer was flushed on the membrane covered beads at a flowrate between 50 μL/min and 200 μL/min. Then sequentially the ligand and the GTPγS-TR were dispensed at the previously set flowrate, with a small resting and incubation interval time. Finally, a washing step at was performed at the same flowrate.

For the immunostaining experiments the chip was then connected to the syringe pump with the following configuration: 1—Immunostaining activation buffer, 2—Ligand, 3—Primary antibody, 4—Secondary antibody, 5—Microfluidic chip, 6—Wash buffer. First the primary antibody solution was flushed on the membrane covered beads at a flowrate between 50 μL/min and 100 μL/min then at a decreased flowrate between 2 μL/min and 50 μL/min. A washing step was then done with between 50 μL/min and 200 μL/min. The secondary antibody was then added in the same way as the primary antibody. Once the staining achieved the activation steps were done by adding sequentially the immunostaining activation buffer between 50 μL/min and 300 μL/min and then the ligand at the same flowrate. Finally, two washing steps were performed with the immunostaining activation buffer separated by a small incubation time.

Results

Figure 10:
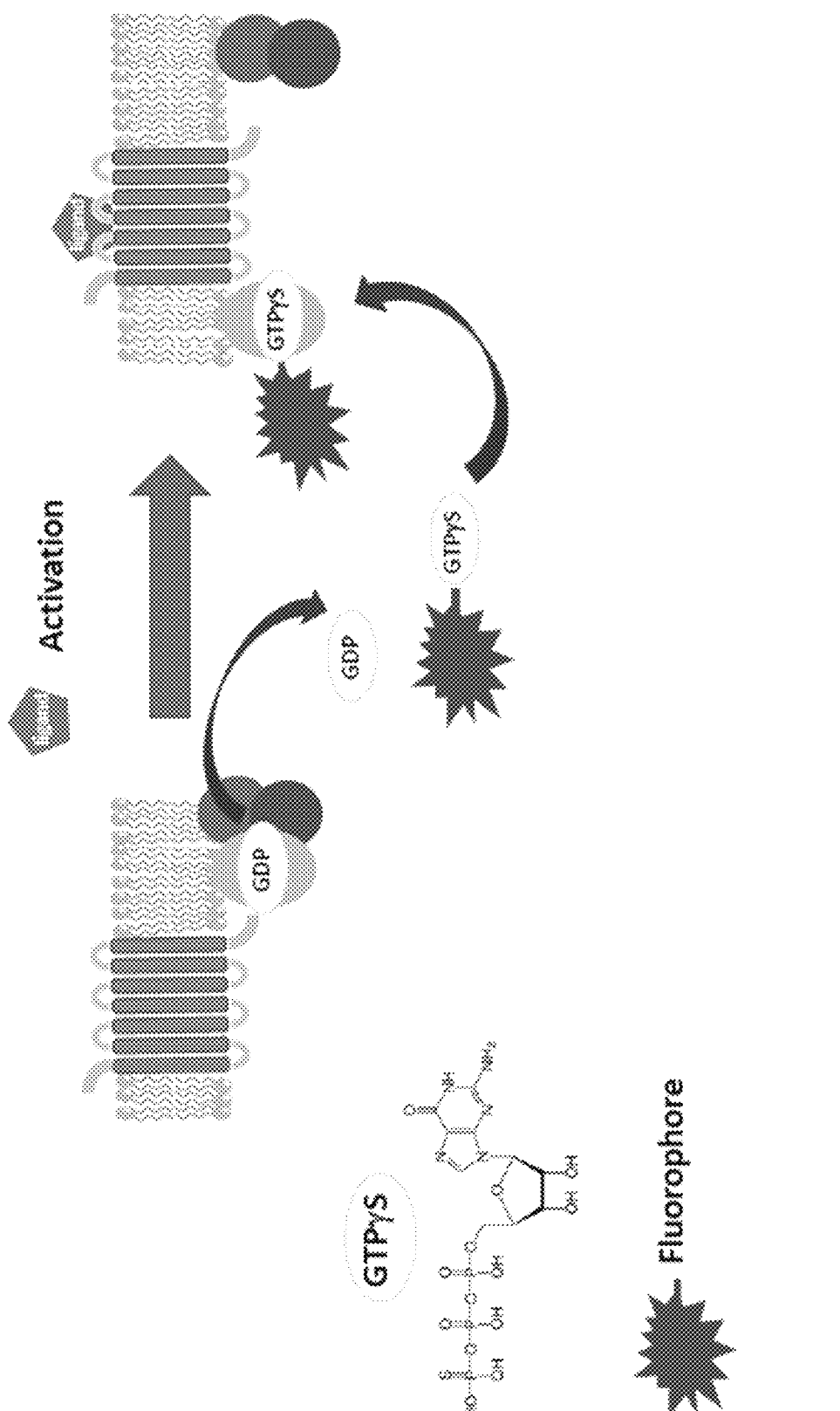
FIG. 10. Schematic representation of the fluorescently labelled GTPγS assay.
Figure 11:
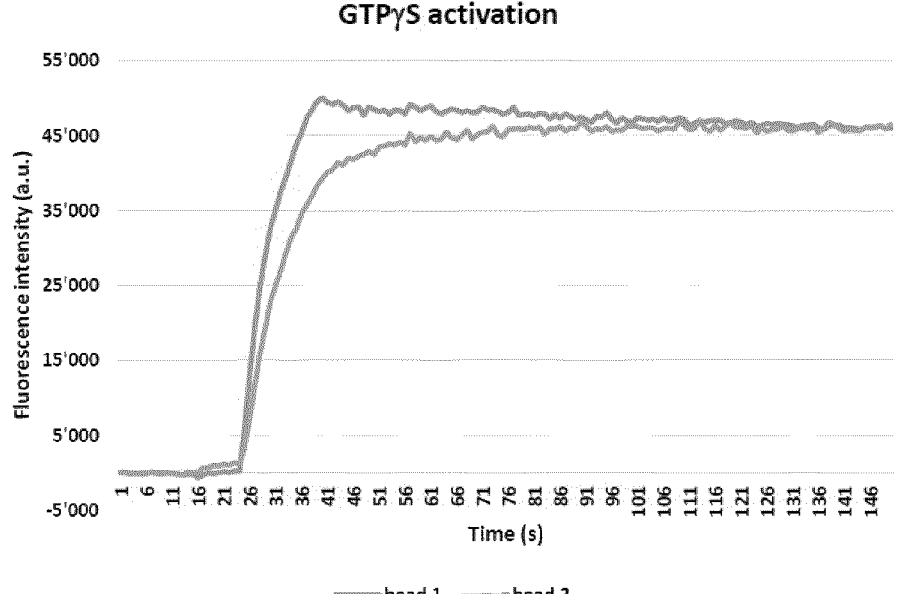
FIG. 11. Fluorescently labeled GTPγS assay on cell membrane coated-beads. Cell membranes were immobilized on the beads and a GPCR, the b2 adrenergic receptor, has been activated by its agonist, the isoproterenol, then we measured the GDP/bodipy-TR-GTPγS exchange with a fluorescent microscope before filling the chip with the bodipy-TR-GTPγS, confocal micrograph B, and after 15 s of a flow of bodipy-TR-GTPγS, confocal micrograph C, scale bars: 60 mm. A) Graph showing the fluorescence increase of bodipy-TR-GTPγS on the beads after the b2 adrenergic receptor activation (unspecific fluorescent background has been removed from the data).
Figure 11:
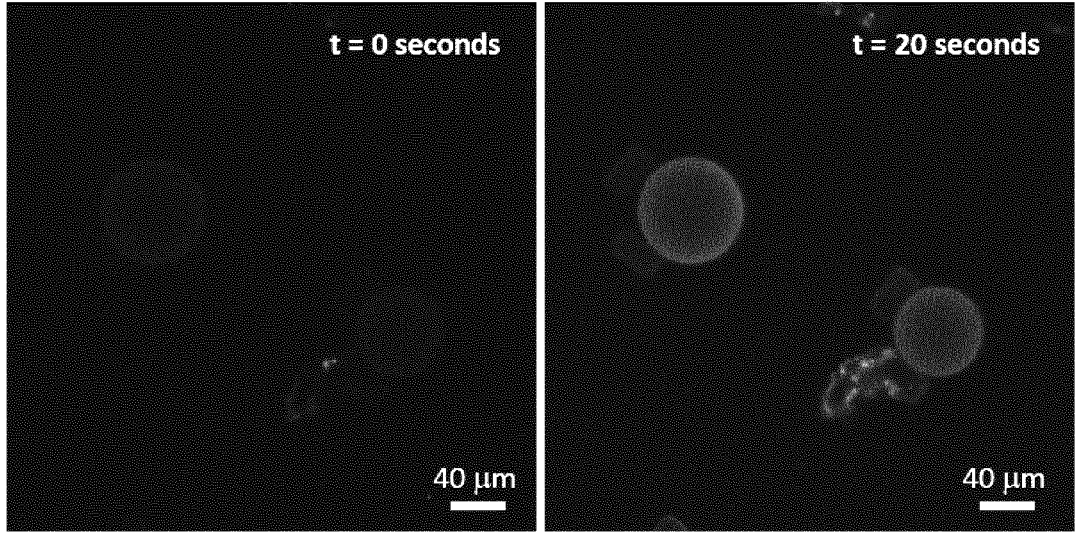

To validate the new screening platform in a microfluidic device, the inventors decided to test a conventional method, the fluorescent GTPγS assay, in the chip. A fluorescently labelled non-hydrolysable GTP analogue binds to the G protein when the GPCR of interest is activated and a substantial fluorescence increase is observed (FIG. 10). After filling the chip with the cell membrane coated-beads, an agonist of the β2 adrenergic receptor, isoproterenol, was introduced in the same chip. Then, the fluorescent GTPγS is loaded in the chip, where it can be observed an increase of fluorescence after few seconds.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

REFERENCES

1. Fredriksson, R. The G-Protein-Coupled Receptors in the Human Genome Form Five Main Families. Phylogenetic Analysis, Paralogon Groups, and Fingerprints. *Mol. Pharmacol.* 63, 1256-1272 (2003).
2. Husted, A. S., Trauelsen, M., Rudenko, O., Hjorth, S. A. & Schwartz, T. W. GPCR-Mediated Signaling of Metabolites. *Cell Metab.* 25, 777-796 (2017).
3. Insel, P. A., Tang, C.-M., Hahntow, I. & Michel, M. C. Impact of GPCRs in clinical medicine: Monogenic diseases, genetic variants and drug targets. *Biochim. Biophys. Acta BBA—Biomembr.* 1768, 994-1005 (2007).
4. Hopkins, A. L. & Groom, C. R. The druggable genome. *Nat. Rev. Drug Discov.* 1, 727-730 (2002).
5. Jacoby, E., Bouhelal, R., Gerspacher, M. & Seuwen, K. The 7?TM G-Protein-Coupled Receptor Target Family. *ChemMedChem* 1, 760-782 (2006).
6. Wu, V. et al. Illuminating the Onco-GPCRome: Novel G protein-coupled receptor-driven oncocrine networks and targets for cancer immunotherapy. *J. Biol. Chem.* 294, 11062-11086 (2019).
7. Hauser, A. S., Attwood, M. M., Rask-Andersen, M., Schiöth, H. B. & Gloriam, D. E. Trends in GPCR drug discovery: new agents, targets and indications. *Nat. Rev. Drug Discov.* 16, 829-842 (2017).
8. Alexander, S. P. et al. THE CONCISE GUIDE TO PHARMACOLOGY 2017/18: G protein-coupled receptors: THE CONCISE GUIDE TO PHARMACOLOGY 2017/18: G protein-coupled receptors. *Br. J. Pharmacol.* 174, S17-S129 (2017).
9. Gilman, A. G. G proteins: transducers of receptor-generated signals. *Annu. Rev. Biochem.* 56, 615-649 (1987).
10. Rodbell, M. The role of hormone receptors and GTP-regulatory proteins in membrane transduction. *Nature* 284, 17-22 (1980).
11. Weis, W. I. & Kobilka, B. K. The Molecular Basis of G Protein-Coupled Receptor Activation. *Annu. Rev. Biochem.* 87, 897-919 (2018).

12. Cabrera-Vera, T. M. et al. Insights into G Protein Structure, Function, and Regulation. *Endocr. Rev.* 24, 765-781 (2003).

13. Milligan, G. & Kostenis, E. Heterotrimeric G-proteins: a short history: Heterotrimeric G-proteins: a short history. *Br. J. Pharmacol.* 147, S46—S55 (2009).

14. Oldham, W. M. & Hamm, H. E. Heterotrimeric G protein activation by G-protein-coupled receptors. *Nat. Rev. Mol. Cell Biol.* 9, 60-71 (2008).

15. Denis, C., Saulière, A., Galandrin, S., Sénard, J.-M. & Galés, C. Probing heterotrimeric G protein activation: applications to biased ligands. *Curr. Pharm. Des.* 18, 128-144 (2012).

16. Zhang, R. & Xie, X. Tools for GPCR drug discovery. *Acta Pharmacol. Sin.* 33, 372-384 (2012).

17. Salahpour, A. BRET biosensors to study GPCR biology, pharmacology, and signal transduction. *Front. Endocrinol.* 3, (2012).

18. Eglen, R. M. & Reisine, T. Photoproteins: Important New Tools in Drug Discovery. *ASSAY Drug Dev. Technol.* 6, 659-672 (2008).

19. McEwen, D. P., Gee, K. R., Kang, H. C. & Neubig, R. R. Fluorescent BODIPY-GTP Analogs: Real-Time Measurement of Nucleotide Binding to G Proteins. *Anal. Biochem.* 291, 109-117 (2001).

20. Harrison, C. & Traynor, J. R. The [35S]GTPγS binding assay: approaches and applications in pharmacology. *Life Sci.* 74, 489-508 (2003).

21. Schröder, R. et al. Deconvolution of complex G protein-coupled receptor signaling in live cells using dynamic mass redistribution measurements. *Nat Biotechnol* 28, 943-949 (2010).

22. Schröder, R. et al. Applying label-free dynamic mass redistribution technology to frame signaling of G protein-coupled receptors noninvasively in living cells. *Nat. Protoc.* 6, 1748-1760 (2011).

23. Ciambrone, G. J. et al. Cellular Dielectric Spectroscopy: A Powerful New Approach to Label-Free Cellular Analysis. *J. Biomol. Screen.* 9,467-480 (2004).

24. Leung, G. et al. Cellular Dielectric Spectroscopy: A Label-Free Technology for Drug Discovery. *J. Assoc. Lab. Autom.* 10,258-269 (2005).

25. Roizard, S. et al. Activation of G-Protein-Coupled Receptors in Cell-Derived Plasma Membranes Supported on Porous Beads. *J. Am. Chem. Soc.* 133, 16868-16874 (2011).

26. Kleinau, G. et al. Differential Modulation of Beta-Adrenergic Receptor Signaling by Trace Amine-Associated Receptor 1 Agonists. *PLoS ONE* 6, e27073 (2011).

27. Ahn, H. S. et al. Binding of a thrombin receptor tethered ligand analogue to human platelet thrombin receptor. *Mol. Pharmacol.* 51, 350-356 (1997).

28. Bosnyak, S. et al. Relative affinity of angiotensin peptides and novel ligands at AT 1 and AT 2 receptors. *Clin. Sci.* 121, 297-303 (2011).

29. Jo, M. C., Liu, W., Gu, L., Dang, W. & Qin, L. High-throughput analysis of yeast replicative aging using a microfluidic system. *Proc. Natl. Acad. Sci.* 112, 9364-9369 (2015).

30. Carlo, D. D., Wu, L. Y. & Lee, L. P. Dynamic single cell culture array. *Lab. Chip* 6, 1445 (2006).

31. Lee, J., Mena, S. E. & Burns, M. A. Micro-Particle Operations Using Asymmetric Traps. *Sci. Rep.* 9, 1278 (2019).

32. Xu, X., Sarder, P., Li, Z. & Nehorai, A. Optimization of microfluidic microsphere-trap arrays. *Biomicrofluidics* 7, 014112 (2013).

33. Xu, X., Li, Z., Sarder, P., Kotagiri, N. & Nehorai, A. Simultaneous detection of multiple biological targets using optimized microfluidic microsphere-trap arrays. *J. MicroNanolithography MEMS MOEMS* 13, 013017 (2014).

34. Crane, M. M., Clark, I. B. N., Bakker, E., Smith, S. & Swain, P. S. A Microfluidic System for Studying Ageing and Dynamic Single-Cell Responses in Budding Yeast. *PLoS ONE* 9, e100042 (2014).

The invention claimed is:

1. A method for determining the presence of a molecule coupled to the cytoplasmic side of a cellular membrane, wherein the molecule coupled to the cytoplasmic side of a cellular membrane is a protein or multi-protein complex selected from a GαGDP-βγ heterotrimeric G protein, a GαGTP subunit of a G protein, Gβγ subunits of a G protein, and a combination thereof, the method comprising the steps of:

a) providing a plurality of micrometric polymeric beads, each located in a trap of a multi-trap microfluidic device, wherein the micrometric polymeric beads comprise on their surface a molecule capable of interacting and binding to an extracellular cell-membrane molecule;

b) loading a plurality of cells into the microfluidic device, wherein the cells adhere to the micrometric polymeric beads through the interaction and binding between the molecule on the surface of the micrometric polymeric beads and the extracellular cell-membrane molecule;

c) breaking the bead-attached cells to expose cellular plasma membrane fragments on the beads in an inside-out orientation;

d) loading into the microfluidic device a labelling compound specific for the molecule coupled to the cytoplasmic side of a cellular membrane, wherein the labelling compound comprises a radioactive probe, a chemiluminescent probe, and/or a fluorescent probe; and e) detecting a radioactive, chemiluminescent, and/or a fluorescent signal associated with the presence of the labelling compound, wherein the signal is indicative of the presence of the molecule coupled to the cytoplasmic side of a cellular membrane;

wherein the multi-trap microfluidic device comprises a plurality of shifted arrays of traps, each trap being configured to accommodate only one bead, and wherein each trap of the multi-trap device is composed of two spaced-apart pillar subunits rotated to create a V shape.

2. The method of claim 1, wherein the cells are mammalian cells.

3. The method of claim 1, wherein the micrometric polymeric beads have a diameter comprised between 5 and 70 μm.

4. The method of claim 1, wherein the molecule coupled to the cytoplasmic side of a cellular membrane is a GαGDP subunit of a G protein, and wherein the method further comprises a step of contacting the cellular plasma membrane fragments on the beads with a molecule to be tested for an agonistic or antagonistic activity on a G protein-coupled receptor i) wherein detection of a radioactive, chemiluminescent and/or a fluorescent signal after the removal of the loaded labelling compound specific for a molecule coupled to the cytoplasmic side of a cellular membrane is indicative of the presence of the GαGDP subunit of a G protein, and therefore a lack of agonistic or antagonistic activity of the tested molecule to be tested for an agonistic or antagonistic activity on a G protein-coupled receptor.

5. A kit comprising a multi-trap microfluidic device, a plurality of micrometric polymeric beads and instructions to perform a method according to claim 1, wherein the multi-trap microfluidic device comprises a plurality of shifted arrays of traps, each trap being configured to accommodate only one micrometric polymeric bead, and wherein each trap of the multi-trap microfluidic device is composed of two spaced-apart pillar subunits rotated to create a V shape.

6. A kit according to claim 5, further comprising a labelling compound specific for a molecule coupled to the cytoplasmic side of a cellular membrane.

7. A kit according to claim 5, wherein the micrometric polymeric beads comprise on their surface a molecule capable of interacting and binding to an extracellular cell-membrane molecule.

8. A kit according to claim 5, wherein the micrometric polymeric beads have a diameter comprised between 5 and 70 μm.

9. The method of claim 1, wherein the molecule capable of interacting and binding to the extracellular cell-membrane molecule is a lectin.

10. The method of claim 1, wherein the pillars are rectangular.

11. The method of claim 1, wherein each subunit of the V shaped trap is spaced 20 μm at the narrowest end and 62 μm at the widest end of the V.

12. The method of claim 1, wherein the plurality of micrometric polymeric beads is loaded into the microfluidic device at a flowrate of from 100 μL/min to 1 mL/min, the plurality of cells is loaded into the microfluidic device at a flowrate between 50 μL/min and 100 μL/min, and the bead-attached cells are broken through a lysis buffer loaded into the microfluidic device at a flowrate up to 200 μL/min.

13. The method of claim 1, wherein the two spaced-apart pillar subunits are present at 45° to create the V shape.

14. The kit of claim 5, wherein the two spaced-apart pillar subunits are present at 45° to create the V shape.

\* \* \* \* \*